(12) United States Patent
DeWoolfson et al.

(10) Patent No.: US 12,102,598 B2
(45) Date of Patent: *Oct. 1, 2024

(54) DEVICES AND METHODS FOR CORNEA TREATMENT

(71) Applicant: D&D Biopharmaceuticals, Inc., Sterling, VA (US)

(72) Inventors: Bruce H. DeWoolfson, Sterling, VA (US); Dale P. DeVore, Chelmsford, MA (US); Michael Luttrell, Dayton, OH (US); Chris L. Davis, Escondido, CA (US)

(73) Assignee: D&D Biopharmaceuticals, Inc., Sterling, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,261

(22) Filed: Feb. 16, 2024

(65) Prior Publication Data

US 2024/0189188 A1    Jun. 13, 2024

Related U.S. Application Data

(63) Continuation of application No. 18/072,163, filed on Nov. 30, 2022, now Pat. No. 11,938,092.

(51) Int. Cl.
*A61J 1/20*     (2006.01)
*A61F 9/00*     (2006.01)

(52) U.S. Cl.
CPC ........... *A61J 1/2093* (2013.01); *A61F 9/0008* (2013.01)

(58) Field of Classification Search
CPC .... A61F 9/0008; A61F 9/0017; A61F 9/0026; B05C 17/01; B05C 17/00553;
(Continued)

(56) References Cited

U.S. PATENT DOCUMENTS

| 2,754,590 A | 9/1954 | Cohen |
| 3,684,136 A | 8/1972 | Baumann |

(Continued)

FOREIGN PATENT DOCUMENTS

| EP | 0700363 B1 | 7/2001 |
| WO | 0035427 A1 | 6/2000 |

(Continued)

OTHER PUBLICATIONS

Ritter, A. et al., "An Eye on the Future of Preservative-Free Drops," ONdrugDelivery, Issue 130, pp. 20-26, Mar. 14, 2022, available at https://www.ondrugdelivery.com/an-eye-on-the-future-of-preservative-free-drops/.

(Continued)

*Primary Examiner* — Adam Marcetich
(74) *Attorney, Agent, or Firm* — Bookoff McAndrews, PLLC

(57) ABSTRACT

Medical devices and methods of use thereof are described. The device may include a body having a housing that defines a lumen, a piston within the housing, and an actuator operably coupled to the piston, wherein the piston is movable along the lumen by operating the actuator. The device also may include a cartridge insertable into the body and/or a flexible fitting configured for direct application to an eye of a subject.

16 Claims, 11 Drawing Sheets

(58) Field of Classification Search
CPC ........ B05C 17/00576; B05C 17/00596; B05C 17/0123; B05C 17/015; B05C 17/00583; A61M 5/31581; A61M 5/24; A61M 2210/0612; A61M 5/284; A61M 5/31511; A61M 5/14546; A61M 5/1452; A61M 5/19; A61M 5/20; A61M 5/3158; A61M 5/31595; A61M 2005/2407; A61M 25/10182; B65D 83/0005; B65D 81/3255; B65D 83/0072; B65D 47/10; B65D 81/325

See application file for complete search history.

(56) References Cited

U.S. PATENT DOCUMENTS

| | | | |
|---|---|---|---|
| 3,906,949 | A | 9/1975 | Holland |
| 4,208,133 | A | 6/1980 | Korte-Jungermann |
| 4,472,141 | A | 9/1984 | Dragan |
| 4,632,669 | A | 12/1986 | Phipps, Sr. et al. |
| 4,696,612 | A | 9/1987 | Germond et al. |
| 4,713,446 | A | 12/1987 | DeVore et al. |
| 4,851,513 | A | 7/1989 | DeVore et al. |
| 4,898,588 | A | 2/1990 | Roberts |
| 5,067,961 | A | 11/1991 | Kelman et al. |
| 5,151,093 | A * | 9/1992 | Theeuwes ............ A61M 5/155 604/218 |
| 5,219,895 | A | 6/1993 | Kelman et al. |
| 5,290,228 | A | 3/1994 | Uemura et al. |
| 5,332,802 | A | 7/1994 | Kelman et al. |
| 5,476,515 | A | 12/1995 | Kelman et al. |
| 5,480,427 | A | 1/1996 | Kelman et al. |
| 5,631,243 | A | 5/1997 | Kelman et al. |
| 5,704,918 | A | 1/1998 | Higashikawa |
| 5,951,565 | A | 9/1999 | Freeman |
| 5,992,694 | A | 11/1999 | Keller |
| 6,089,412 | A | 7/2000 | Snell et al. |
| 6,161,544 | A | 12/2000 | DeVore et al. |
| 6,183,498 | B1 | 2/2001 | DeVore et al. |
| 6,260,737 | B1 | 7/2001 | Gruendeman |
| 6,299,856 | B1 | 10/2001 | DeVore et al. |
| 6,386,872 | B1 | 5/2002 | Mukasa et al. |
| 6,598,764 | B1 | 7/2003 | Stern |
| 6,743,435 | B2 | 6/2004 | DeVore et al. |
| 6,946,440 | B1 | 9/2005 | DeWoolfson et al. |
| 7,402,562 | B2 | 7/2008 | DeWoolfson et al. |
| 7,824,372 | B1 | 11/2010 | Kurup |
| 8,221,353 | B2 | 7/2012 | Cormier et al. |
| 8,672,904 | B1 | 3/2014 | Schultz |
| 9,198,673 | B2 | 12/2015 | Stone |
| 9,399,102 | B2 | 7/2016 | DeWoolfson et al. |
| 10,342,697 | B2 | 7/2019 | Friedman et al. |
| 11,259,959 | B1 | 3/2022 | DeWoolfson et al. |
| 2001/0047153 | A1 | 11/2001 | Trocki et al. |
| 2002/0035351 | A1 | 3/2002 | Lodice |
| 2003/0060763 | A1 | 3/2003 | Penfold et al. |
| 2003/0065293 | A1 | 4/2003 | Hess |
| 2005/0106270 | A1 | 5/2005 | DeVore et al. |
| 2005/0137575 | A1 | 6/2005 | Thompson et al. |
| 2005/0252795 | A1 | 11/2005 | Peuker et al. |
| 2007/0265579 | A1 | 11/2007 | Kleyman et al. |
| 2009/0082776 | A1 | 3/2009 | Cresina |
| 2009/0105127 | A1 | 4/2009 | Thomspon et al. |
| 2010/0106097 | A1 | 4/2010 | Elmouelhi |
| 2011/0060267 | A1 | 3/2011 | DeWoolfson et al. |
| 2011/0086802 | A1 | 4/2011 | DeWoolfson et al. |
| 2011/0264033 | A1 | 10/2011 | Jensen et al. |
| 2011/0282305 | A1 | 11/2011 | Welser |
| 2012/0057121 | A1 | 3/2012 | DeWoolfson et al. |
| 2012/0265171 | A1 | 10/2012 | Thorne, Jr. et al. |
| 2013/0237935 | A1 | 9/2013 | Kouyoumijan et al. |
| 2014/0034670 | A1 | 2/2014 | Cheetham |
| 2014/0048556 | A1 | 2/2014 | Pearcy et al. |
| 2014/0081205 | A1 | 3/2014 | Kanner et al. |
| 2015/0057608 | A1 | 2/2015 | Hitscherich, Jr. et al. |
| 2016/0000885 | A1 | 1/2016 | Thompson et al. |
| 2016/0008779 | A1 | 1/2016 | Seaward et al. |
| 2016/0058988 | A1 | 3/2016 | Kesten et al. |
| 2016/0243343 | A1 | 8/2016 | Miller |
| 2016/0270956 | A1 | 9/2016 | Lin et al. |
| 2017/0007772 | A1 | 1/2017 | Nemoto et al. |
| 2017/0189229 | A1 | 7/2017 | Hardten et al. |
| 2018/0117253 | A1 | 5/2018 | Salahshoor Kordestani |
| 2018/0132919 | A1 | 5/2018 | Vogt et al. |
| 2018/0140461 | A1 | 5/2018 | Nandigala et al. |
| 2018/0169694 | A1 | 6/2018 | Baylis |
| 2019/0216830 | A1 | 7/2019 | Higuchi et al. |
| 2020/0121769 | A1* | 4/2020 | Chang ................ A61K 9/0014 |
| 2020/0188597 | A1 | 6/2020 | Gagliano |
| 2021/0069426 | A1 | 3/2021 | Huculak et al. |
| 2022/0088314 | A1 | 3/2022 | Knorr et al. |

FOREIGN PATENT DOCUMENTS

| | | |
|---|---|---|
| WO | 2009120549 A2 | 10/2009 |
| WO | 2021136820 A1 | 7/2021 |

OTHER PUBLICATIONS

International Search Report for PCT/US2023/081601 dated Mar. 28, 2024 (5 pages).

* cited by examiner

DEVICES AND METHODS FOR CORNEA TREATMENT

CROSS-REFERENCE TO RELATED APPLICATIONS

This application is a continuation of U.S. application Ser. No. 18/072,163 filed on Nov. 30, 2022, which is incorporated by reference herein in its entirety.

TECHNICAL FIELD

The present disclosure is directed to devices for delivering compositions to an eye of a subject, e.g., in preparation for, during, and/or after a medical procedure.

BACKGROUND

The corneal epithelium is the outermost tissue layer of the cornea and serves to protect the eye from intrusions of foreign substances into the underlying tissue structures. The epithelium is four to five cell layers in thickness and the junctures between the cells in each layer are tightly connected. The tight protective shield of the epithelium makes it difficult to introduce desired agents into the cornea, such as antibiotics to fight an infection, dilating agents to open the pupil to permit examination of the retina, or other therapeutic or pharmaceutical agents.

The treatment of many ophthalmic diseases and post-operative conditions require frequent administration of drugs to the ocular tissues. Many medications must be applied topically to the eye, and one common form of treatment is the use of drops or ointments. The topical formulation is administered by the patient or caregiver using an eye dropper or dispenser. However, a substantial disadvantage of this method of drug delivery is that the medication can rapidly drain from the ocular surface into the lacrimal system through an opening in the eyelid called the punctum. Furthermore, the medication can be rapidly diluted by tears secreted by the lacrimal gland, and preservatives in multi-dose bottles can cause irritation or more serious complications to ocular tissues. Another approach for localized drug delivery involves the injection of the drug directly under the conjunctiva or Tenon capsule, intracamerally or intra-vitreally. This approach can require periodic injections of the drug to maintain an effective concentration at the target site and has many potential adverse effects. Current treatment methods like these can result in sporadic delivery of medication with unpredictable dosage at the target tissue. Intermittent administration can also lead to an initial over-dosage with a rapid decrease in concentration to ineffective levels, due to dilution and lacrimal drainage.

SUMMARY

The present disclosure includes medical devices useful for ocular procedures and methods of use thereof, e.g., to treat a subject. For example, the present disclosure includes a method device comprising: a body including a housing that defines a lumen, a piston within the housing, and an actuator operably coupled to the piston, wherein the piston is movable along the lumen by operating the actuator; a cartridge insertable into the lumen, wherein a distal end of the cartridge is sealed with a pierceable material; and a flexible fitting configured for direct application to an eye of a subject, the fitting being coupled to, and removable from, the cartridge or a distal end of the housing of the body. The body may include a handle extending along an axis transverse to the lumen, the handle including the actuator. Additionally or alternatively, the body may include a slot in communication with the lumen, the cartridge being removable from the lumen through the slot. In some examples herein, a proximal end of the fitting includes mating elements complementary to mating elements of the cartridge or mating elements of the distal end of the housing. Optionally, the device may further include a motor proximate the lumen and capable of shaking the cartridge when the cartridge is disposed within the lumen. In some examples, the device does not include electronic components. The device may include a release button to re-set a starting position of the piston.

Accordingly to some aspects of the present disclosure, the pierceable material of the cartridge comprises metallic foil or polymeric film. Further, for example, a proximal end of the cartridge may be sealed with an element that includes a piercing tip extending toward the distal end of the cartridge. In some examples, the cartridge includes a first subcartridge proximal to a second subcartridge, a distal end of the second subcartridge being sealed with the pierceable material. A distal end of the first subcartridge may be sealed with a pierceable material. Additionally or alternatively, the first subcartridge may contain a liquid and/or the second subcartridge may contain a powder.

An exemplary method of treating a subject using a device as described above and/or elsewhere herein comprises: preparing a composition by combining the liquid with the powder by pressing the actuator to move the piston distally to establish fluid communication between the first subcartridge and the second subcartridge, wherein moving the piston distally breaks a pierceable material between the first and second subcartridges, and wherein the liquid comprises a buffer solution and the powder comprises an acylating agent; mixing the composition; placing the fitting against an eye of the subject; and administering the composition to the eye by expelling the composition into an enclosed space between the fitting and the eye. According to some aspects of the present disclosure, the first subcartridge further comprises an active agent mixed with the buffer solution, wherein the second active agent comprises a steroid, an anti-inflammatory agent, an antihistamine, a prostaglandin, an anesthetic agent, or an antimicrobial agent.

The present disclosure also includes a medical device comprising a body, the body including: a housing that defines a lumen and a slot in communication with the lumen, the slot being (a) between a proximal end of the housing and a distal end of the housing or (b) at a distal end of the housing; a piston disposed within the lumen; and an actuator operably coupled to the piston, wherein the piston is movable along the lumen by operating the actuator. In some examples, the device further comprises a cartridge insertable into the lumen through the slot. For example, a distal end of the cartridge may be sealed with a pierceable material, and a proximal end of the cartridge may be sealed with an element that includes a piercing tip extending toward the distal end of the cartridge. The cartridge may include a first subcartridge proximal to a second subcartridge, a distal end of the second subcartridge being sealed with the pierceable material and a proximal end of the first subcartridge being sealed with the element. In some examples, the first subcartridge contains a buffer solution and/or the second subcartridge contains an acylating agent. Optionally, the device may further comprise a flexible fitting configured for direct application to an eye of a subject. The fitting may be coupled to, and removable from, a distal end of the cartridge or a distal end of the housing of the body via complementary mating elements. According to some aspects, a proximal end of the cartridge includes at least one tab, and the slot of the housing includes at least once recess corresponding to each tab.

The present disclosure also includes a method of treating a subject using a medical device comprising a housing and a flexible fitting, wherein the housing defines a lumen that contains a cartridge and a piston operably coupled to an actuator, and wherein the cartridge includes a first subcartridge that contains a buffer solution and a second subcartridge that contains an active agent. The method may comprise preparing a composition by combining the buffer solution with the active agent by pressing an actuator of the device to move the piston distally to establish fluid communication between the first subcartridge and the second subcartridge; mixing the composition; placing the fitting against an eye of the subject, wherein the fitting flares radially outward to accommodate a convex curvature of the eye; and administering the composition to the eye by expelling the composition into an enclosed space between the fitting and the eye. In some examples, the active agent is an acylating agent and the composition is administered to the eye while having a pH ranging from about 8.4 to about 8.6. Further, for example, the active agent may be a first active agent and the first subcartridge may further comprise a second active agent mixed with the buffer solution. For example, the second active agent may comprise a steroid, an anti-inflammatory agent, an antihistamine, a prostaglandin, an anesthetic agent, or an antimicrobial agent. In some examples herein, the composition does not comprise a preservative. Establishing fluid communication between the first subcartridge and the second subcartridge may include piercing a thin foil or polymeric film between the first subcartridge and the second subcartridge. The method may further comprise inserting the cartridge into the lumen before preparing the composition, and removing the cartridge from the lumen after administering the composition to the eye.

It is to be understood that both the foregoing general description and the following detailed description are exemplary and explanatory only and are not restrictive of the present disclosure, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
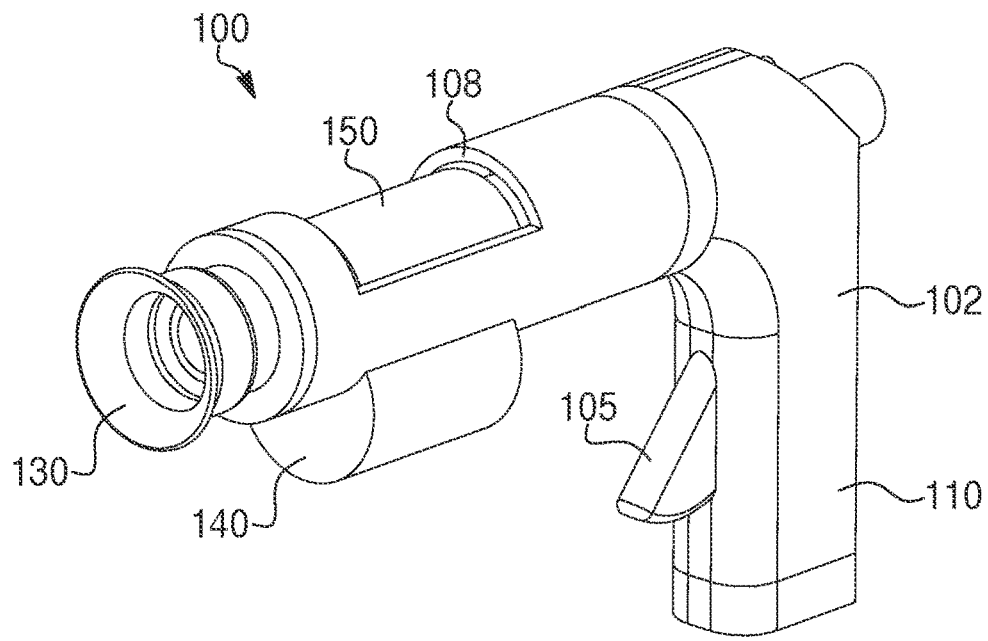
FIG. 1 is a perspective view of an exemplary medical device according to some aspects of the present disclosure.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass±5% of a specified amount or value. Any aspect described herein as exemplary is not to be construed as preferred or advantageous over other aspects. Rather, the term "exemplary" is used in the sense of example or illustrative.

The devices herein may provide for effective and controlled delivery of therapeutic agents, including pH-sensitive agents, to one or both eyes of a subject, e.g., a human subject such as a patient. For example, the devices and methods described herein may be useful for delivering agents to a subject's eyes before, during, and/or after an ocular examination or other procedure. The devices herein may be useful for agents prepared from multiple components that are mixed before application to the eye and applied to the eye within a desired pH range. Mixing components in real time to achieve a composition within the desired pH range may aid in promoting a safe and comfortable experience for the subject.

According to some examples herein, the device may be used to combine components or ingredients housed within a cartridge to prepare a therapeutic composition (which may comprise one or more active agents), and deliver the composition to a subject's eye(s). Generally, the device may comprise a body including a housing that defines a lumen and a piston movable along the lumen by operating an actuator. The device also may include a cartridge insertable into, and removable from, the lumen. For example, the cartridge may be single-use and disposable, e.g., the cartridge containing one or more therapeutic agents, such as one or more active agents. The device also may include a flexible fitting configured for direct application to an eye of a subject, wherein the fitting may be integral with the body or may be removably coupled to the body or to the cartridge. For example, the fitting may be single-use or otherwise replaceable/exchangeable. Different fittings may be used to accommodate different subjects, for example. The distal end of the fitting may have a size and shape to accommodate the convex curvature of the eye. The fitting may comprise a suitable biocompatible material able to confer flexibility for comfort of the subject when the fitting contacts the eye. For example, the fitting may comprise silicone, rubber, plastic, or other polymers.

The body may include a handle. For example, the handle may have a shape able to be grasped by a user in order to operate the actuator and/or position the device to deliver a composition to a subject's eye. In some aspects of the present disclosure, the handle may extend along an axis transverse to the lumen of the body, e.g., forming approximately a right angle with the lumen or an angle between about 90 degrees and about 135 degrees. In other aspects, the handle may extend along the same axis as the lumen. Optionally, the handle may include a power source such as a battery (e.g., a rechargeable battery) and/or an electronic connector configured to receive power from an external power source. Further, for example, the handle may include a processor, e.g., included in a circuit board, for controlling one or more electronic components of the device as discussed further below. In some examples, however, the device does not include electronic components.

The actuator of the device may engage a piston disposed with the lumen to move the piston along the lumen. When a cartridge is inserted in the lumen of the body, movement of the piston in a distal direction may likewise move the cartridge and/or components thereof distally, to ultimately deliver a composition (e.g., therapeutic composition) from the cartridge through the fitting to exit the device. In some examples, the device includes a mechanism capable of providing a shaking motion to agitate the lumen and a cartridge disposed within the lumen to promote mixing of therapeutic agent(s) contained within the cartridge.

The piston may be configured to engage the cartridge and advance the cartridge distally in order to deliver a composition contained within the cartridge. In some examples, the composition may exit through one or more openings at or proximate the distal end of the body to exit the device through the fitting. For example, the distal end of the cartridge may include a pierceable material, such as a thin foil or polymeric film. The material may be punctured by sharp inner edges of the opening(s) to allow the composition (e.g., a liquid composition) to exit the device through the opening(s). In other examples, the composition may exit the cartridge through the fitting (e.g., the fitting being coupled to the cartridge, both the fitting and the cartridge being distal to the body). The distal end of the cartridge may include a pierceable material that is punctured by a piercing tip of a pierceable element within the cartridge.

In some examples, the cartridge includes a single chamber. For instance, the cartridge may be provided as a sealed container with the composition therein.

In other examples, the cartridge may include two or more subcartridges with components of a composition to be mixed together using the device before the composition exits the device for administration to a subject. The piston may be configured to advance the two or more cartridges sequentially in order to mix the components together. The two or more subcartridges may contain different active agents and/or other components of a composition, each subcartridge being sealed prior to use to avoid contamination or other environmental exposure. For example, the subcartridges may have one or more openings sealed by a material such as a metal, metal alloy, or polymer. In order to combine components, the material may be pierced or otherwise punctured to allow for components to mix together. For example, a first movement of the piston against the cartridge may cause a first, proximal subcartridge to push against a second, distal subcartridge and thereby puncture a distal seal of the first subcartridge and a proximal seal of the second subcartridge. Puncturing the respective seals may allow for the contents of the two subcartridges to mix within the cartridge.

Further movement of the piston may move both the first and second subcartridges relative to the body of the device. When the distal end of the cartridge (e.g., corresponding to the distal end of the second subcartridge) contacts sharp features of the body of the device, the sharp feature may pierce the material of the distal end of the cartridge to allow a composition therein to exit the cartridge and the device. Alternatively, further movement of the piston may pierce the distalmost end of the cartridge to allow the composition to exit the cartridge.

As mentioned above, the devices herein optionally may include a mechanism to promote mixing of the contents of a cartridge when disposed within the lumen. The mechanism may be proximate the lumen. For example, the mechanism may be housed in a chamber adjacent to the lumen, such as a chamber that shares a wall with the lumen. In some examples, the mechanism includes a motor, e.g., a vibratory motor. The motor or other mechanism may be controlled manually by the user, may be initiated based on a predetermined algorithm (e.g., an algorithm saved within memory/circuitry of the device), or may be engaged based on movement of the piston. For example, the piston may advance along the lumen a sufficient distance to cause two electrical contacts to touch each other and initiate the motor. Further movement of the piston may separate the electrical contacts and deactivate the motor.

According to some aspects of the present disclosure, the device may be programmed to perform sequential steps upon initiation of the actuator. For example, movement of the piston may be automated. A user may activate the actuator, wherein the piston moves to the first position. The device may then wait a predetermined amount of time and move the piston into the second position without a second activation of the actuator by the user. Parameters of an automated method may be programmed in a processor, e.g., of a circuit board of the device.

The device may comprise an indicator to provide information on a status of the device during operation. For example, the device may provide one or more audio and/or visual indicators configured to convey to a user when to perform different actions and/or when a composition is ready to be applied to a subject. In the case of a pH-sensitive composition, for example, an indicator may include a light source that illuminates when the composition has reached an appropriate pH for administration to a subject. The appropriate pH may be determined based on the amount of time after components have been mixed together to initiate a change in pH as a function of time. In at least one example, the device includes a visual indicator in the form of a light source configured to emit a specified color and/or to change color when multiple components of a composition are to be mixed, when mixing begins and/or ends, and/or when a desired pH or pH range has been reached by a composition. For example, the light source may emit red light while components are mixing, and then may change to green light after the components have mixed for a sufficient amount of time.

The devices herein may be used to deliver various therapeutic compositions comprising one or more active agents to a subject's eye(s). The desired active agent(s) and/or composition comprising one or more active agents may be provided within the cartridge, e.g., sealed within the cartridge to avoid contamination or other environmental exposure that may damage, inactivate, or otherwise impair activity of the active agent(s) before administration to the subject. The active agent(s) and composition(s) comprising the active agent(s) may be in liquid or solid form. The cartridge may be formulated for a single-use application, without preservatives that otherwise could cause irritation and/or other harm to the eye.

In some examples, the device may be used to administer a composition prepared from two or more agents contained within separately sealed subcartridges of the cartridge. For example, the cartridge may include a first subcartridge that contains a first agent (e.g., a buffer solution) and a second subcartridge that contains a different, second agent (e.g., an active agent). When combined, the first and second agents may produce a composition for administration to a subject. Optionally, the first and/or second cartridge may comprise multiple agents including multiple active agents. For example, the cartridge may include a first subcartridge that contains a buffer solution and an active agent, and a second subcartridge that contains an active agent different from the active agent of the first subcartridge. When the contents of the two subcartridges are combined during use, the composition formed would comprise a buffer solution and two different active agents.

Exemplary active agents that may be delivered to a subject's eye include acylating agents, which when applied to the cornea may open tight epithelial junctures to permit trans-corneal penetration of pharmaceutical agents and other therapeutic agents. The acylating agent may be combined with a buffer solution using the device to produce a composition with a pH suitable for administration to the eye and open epithelial junctures. The acylating agent and the buffer may be contained in separate subcartridges, wherein operation of the device may combine the acylating agent and buffer to produce the composition.

Acylating agents useful for the present disclosure include anhydrides, acid chlorides, sulfonyl chlorides, and sulfonic acid. Suitable anhydrides include agents that change the net charge from positive to negative. Exemplary anhydrides suitable for the devices and methods herein include, but are not limited to, maleic anhydride, succinic anhydride, glutaric anhydride, citractonic anhydride, methyl succinic anhydride, itaconic anhydride, methyl glutaric anhydride, dimethyl glutaric anhydride, phthalic anhydride, acetic anhydride, chloroacetic anhydride, propionic anhydride, butyric anhydride, isobutyric anhydride, isovaleric anhydride, and hexanoic anhydride. Anhydrides are sensitive to conversion to the corresponding acid (e.g., conversion of glutaric anhydride to glutaric acid) when exposed to and/or mixed with an aqueous solution. Such anhydrides are also reactive with deprotonated amines on protein molecules. Amine groups on protein molecules can be deprotonated by exposure to an alkaline buffer, for example. Exemplary acid chlorides suitable for the devices and methods herein include, but are not limited to, oxalyl chloride, malonyl chloride, acetyl chloride, propionyl chloride, dichloropropionyl chloride, butyryl chloride, isobutyryl chloride, and valeryl chloride. Exemplary sulfonyl chlorides suitable for the devices and methods herein include, but are not limited to, chlorosulfonylacetyl chloride, chlorosulfonylbenzoic acid, 4-chloro-3-(chlorosulfonyl)-5-nitroebnzoic acid, 3-(chlorosulfonyl)-P-anisic acid, ethane sulfonyl chloride, methane sulfonyl chloride, and 1-butane sulfonyl chloride.

Acylation reagents may preferentially react with protein groups, such as lysine groups, that have been deprotonated. These same reagents also have the potential to react with N-terminal amino groups, with tyrosyl residues and cysteinyl residues. Deprotonation of ε-amino groups on lysine may be achieved by increasing the pH to alkaline levels. Effective pH levels for deprotonation of ε-amino groups on lysine is generally around pH 10.0. However, reactions with acylation agents typically occur between pH 8.0 and 9.0, and reactivity is generally slow at pH 7.0. The active acylating agent may react with deprotonated protein(s) to alter the protein solubility. Accordingly, timing is a consideration for effective delivery of acylating agents in an alkaline buffer solution to proteins that have also been exposed to and deprotonated by an alkaline buffer.

Acylation reaction kinetics may depend on (1) reaction pH (e.g., reactions may occur faster at higher pH, such as up to pH 10.0), (2) the concentration of acylation agent, and/or (3) hydrolysis of the acylation agent to an inactive form in aqueous solution (time factor). As discussed above, reactivity is greater at higher pH. When proteins are acylated in solution, the pH is understood to constantly adjust to alkaline pH, for example pH 9.0. The effectiveness of acylation also may depend on the concentration of the active acylation agent. The acylation agent may rapidly hydrolyze into an inactive acid with a concurrent reduction in pH. The acidic form may be inactive, such that as the pH drops, the rate of acylation also drops due to less reactive acylation agent available and lower pH that does not favor reactivity.

The reaction involves a balance between pH and the concentration of active acylation agent. In the case of an anhydride, for example, the ratio of inactive acylation agent (e.g., in acidic form) and active acylation agent (e.g., in anhydride form) changes as soon as the anhydride form is mixed with aqueous solution. The time for complete hydrolysis of anhydride to acid is relatively short, e.g., less than 1 minute. During this time, the pH drops making the active form less reactive. Therefore, both reaction pH and the concentration of active acylation agent are variables to be controlled for effective treatment. The devices herein provide for effective and controlled delivery of pH-sensitive agents to a subject. For example, the devices and methods herein may be useful for creating create trans-epithelial channels for effective delivery of desired therapeutic agents to the eye.

According to some examples herein, a composition formulated for administration to the eye is produced by mixing two components each contained in a respective subcartridge: (1) an acylating agent (e.g., a powdered anhydride) sealed within a subcartridge before use, so that moisture from the air will not degrade the properties of the powder before mixing, and (2) a buffer sealed within a separate airtight subcartridge before use. Exemplary buffer solutions include phosphate buffer, e.g., monobasic sodium phosphate, disodium hydrogen phosphate and/or potassium dihydrogen phosphate, and other alkaline pH buffer solutions such as a carbonate buffer. The buffer may have a pH ranging from about 7.5 to about 9.5, e.g., about 8.0 to about 9.0, or about 8.2 to about 8.5.

To prepare the composition, the acylating agent (e.g., in powder form) and the buffer liquid may be mixed together by placing the two subcartridges in fluid communication with each other, such as by breaking a pierceable material or materials between the two subcartridges. For example, seals between the subcartridges may be pierced by sequential movement of the piston. Contained within a first subcartridge may be a buffer solution, such as an alkaline phosphate buffer. The volume of buffer within the first subcartridge may range from about 250 mL to about 750 mL, e.g., a volume of about 500 mL. Contained within a second subcartridge adjacent to the first subcartridge may be an acylating agent in solid form, e.g., present as a loose powder or as a solid film on an inner surface of the second subcartridge. The amount of acylating agent may range from about 3 mg to about 10 mg, e.g., about 5 mg. In some examples, the acylating agent comprises glutaric anhydride.

As mentioned above, the devices herein may be used to administer various active agents to one or both eyes of a subject. Other exemplary active agents that may be administered with the devices herein include, but are not limited to, riboflavin, steroids, anti-inflammatory agents, antihistamines, prostaglandins, anesthetic agents, and antimicrobial agents (e.g., antifungal agents, antibiotics, antibacterial agents, antiviral agents, etc.). Exemplary active agents that may be delivered using the devices and methods herein include, but are not limited to, riboflavin, timolol, latanoprost (e.g., Xalatan), epinephrine, neosynephrine, phenylephrine, hydroxyamphetamine, tropicamide, cyclopentolate, atropine, homatropine, scopolamine, deflazacort, and prednisone (including prednisone acetate). For example, the cartridge may contain an active agent such as riboflavin, a steroid, an anti-inflammatory agent, an antihistamine, a prostaglandin, an anesthetic agent, or an antimicrobial agent within a buffer solution, In some examples, the cartridge may include two subcartridges, a first sealed subcartridge containing a buffer solution and riboflavin, a steroid, an anti-inflammatory agent, an antihistamine, a prostaglandin, an anesthetic agent, or an antimicrobial agent; and a second sealed subcartridge containing an acylating agent, wherein the device may be used to place the first and second subcartridges in fluid communication to produce a composition of the acylating agent and active agent in buffer solution, which then may be administered to a subject.

Multi-dose containers of medications typically include a preservative to kill pathogens that could be introduced when opening and closing the container, in order to maintain sterility. However, these preservatives such as benzalkonium chloride and other quaternary ammonium chemicals can pose risks to sensitive ocular structures such as corneal and conjunctival epithelial cells. Long-term exposure to preservatives also may roughen the surface of the cornea and conjunctiva. The devices herein provide methods of delivering active agents to the eye without preservatives.

As mentioned above, the devices of the present disclosure may be used to administer a composition prepared from agents contained within separately sealed subcartridges of the cartridge. In some examples, the device may be used to administer a composition comprising two different active agents. The first active agent may be an acylating agent, for example, while the second active agent may be a pharmaceutical agent or other therapeutic agent other than an acylating agent such as, e.g., riboflavin, a steroid, an anti-inflammatory agent, an antihistamine, a prostaglandin, an anesthetic agent, or an antimicrobial agent. As discussed above, the acylating agent may be contained in a different subcartridge of the device than a buffer solution to allow for combining the acylating agent and buffer shortly before administration to the eye to ensure that the composition has the desired pH when applied to the subject. That is, the acylating agent may be contained within a first subcartridge, and the buffer solution may be contained within a second subcartridge. In cases in which a second active agent is administered, the second active agent may be contained within the second subcartridge with the buffer solution. For example, the second active agent may comprise riboflavin, a steroid, an anti-inflammatory agent, an antihistamine, a prostaglandin, an anesthetic agent, or an antimicrobial agent.

Operation of the devices herein as discussed above (and/or as illustrated below with reference to the figures) may combine the contents of the first and second subcartridges to produce a composition comprising the buffer solution, second active agent, and acylating agent. Once the composition is applied to the eye, the acylating agent may open tight epithelial junctures of the cornea to allow the second active agent to pass through the junctures to the intended internal eye tissues for treatment. In this way, the device may permit administration of various active agents without the use of preservatives, using a convenient single-use cartridge pre-loaded with the desired active agent(s). By administering the active agent(s) together with the acylating agent, the subject being treated may experience a more convenient and efficient procedure, avoiding extended office visits and waiting times for the desired therapeutics to take effect.

While the following describes exemplary devices illustrated in the figures used to prepare a composition prepared from two components (e.g., a powder and a liquid, or two liquids, for example), the present disclosure is not limited to these examples. Rather, the devices herein may include additional or fewer components that those shown, as discussed herein, and may be used to deliver other compositions to the eye, including compositions formulated for administration to a subject and having properties that change over time (e.g., viscosity, temperature, etc.).

FIGS. 1-6 depict an exemplary medical device 100 according to the present disclosure, the device including a body 102 defining a lumen 104 and including a handle 110 with an actuator 105. The lumen 104 is in communication with a slot 108 providing access to the lumen 104 between proximal and distal ends of the body 102. The lumen 104 may receive a cartridge 150 through the slot 108, the cartridge 150 being removable and replaceable (see also FIGS. 5 and 6). As shown, the body 102 includes a chamber 140 which may contain a motor 145 proximate the lumen 104 as discussed below. The device 100 also includes a fitting 130 at the distal end of the body 102. In this example, the fitting 130 is removable from the body 102 via complementary engagement elements, but in other examples, the fitting 130 may be integrated into the body 102.

Figure 2:
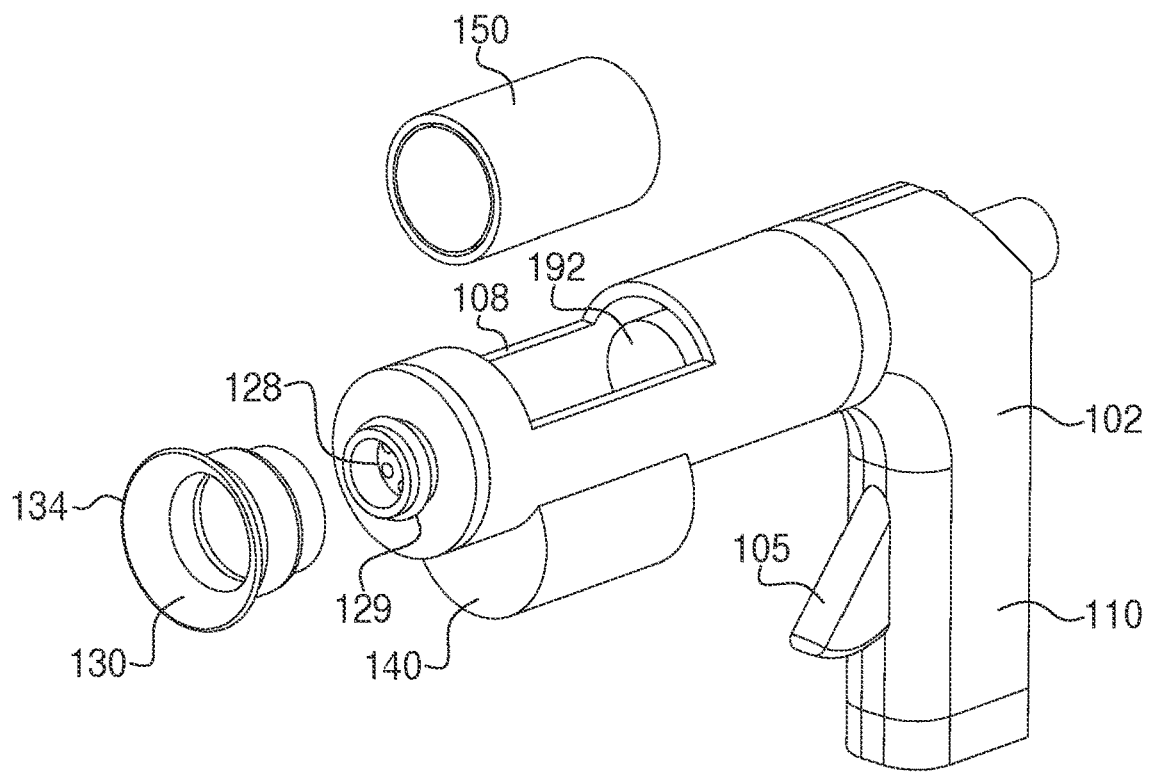
FIGS. 2 and 3 show exploded views of components of the device of FIG. 1.
Figure 3:
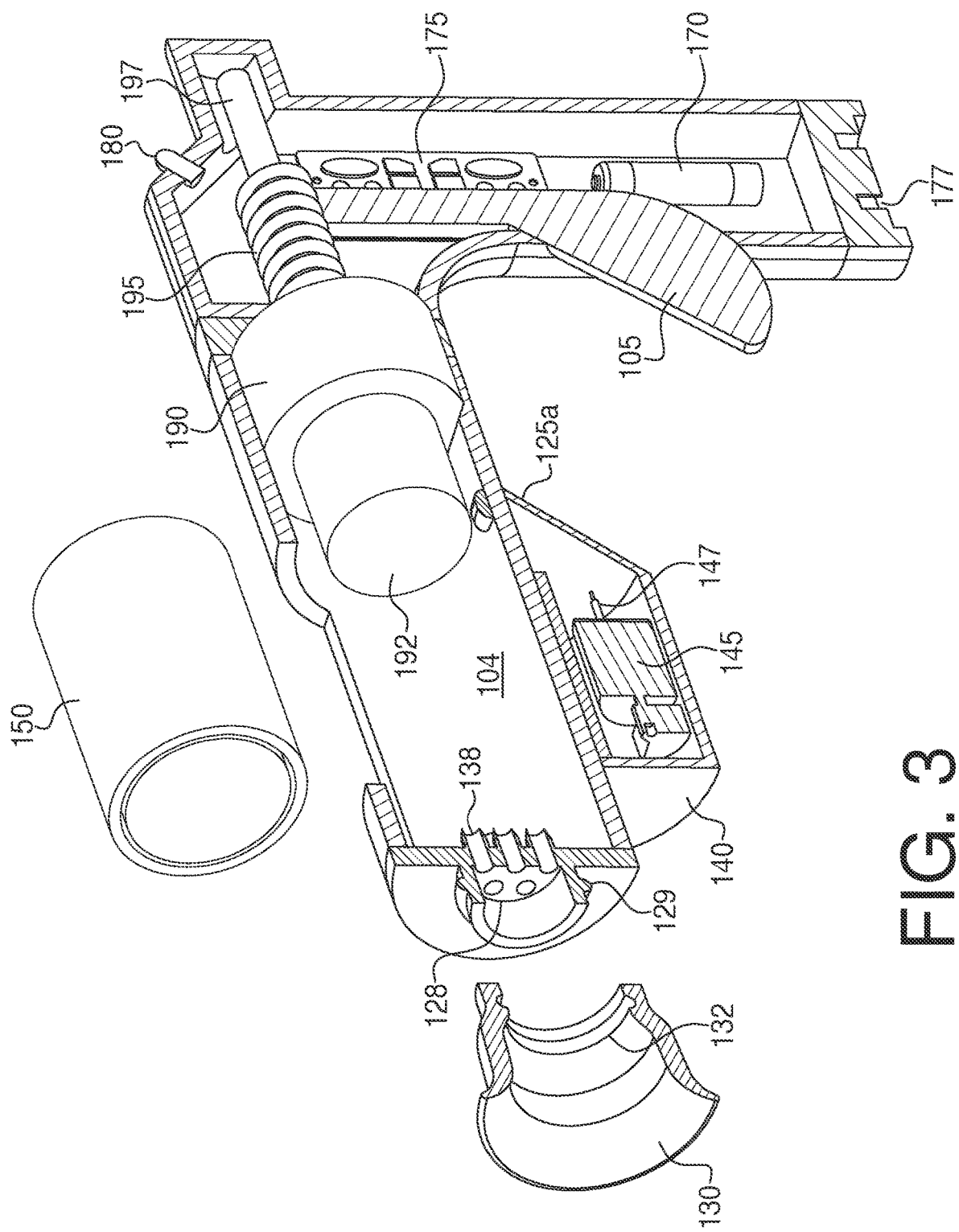

FIGS. 2 and 3 show partially exploded views of the medical device 100, showing cartridge 150 and fitting 130 in this example as removable components. For instance, each of cartridge 150 and fitting 130 may be single-use, replaceable components. The fitting 130 may have engagement elements 132 (see FIG. 3) complementary to engagement elements 129 of the body 102. As shown, the engagement elements 129, 132 include complementary threads (e.g., on the inner surface of fitting and outer surface of body 102 as shown, or vice versa) but other engagement elements such as clips, tabs, friction-fit, Luer-lock connection, magnets, etc. may be used. The fitting 130 has a flared distal end 134 that is able to accommodate the convex curvature of a subject's eye. The cartridge 150 has a generally cylindrical shape to fit within a similarly shaped lumen 104. For example, the cross-sectional dimension (diameter in this example) of the cartridge 150 may be slightly smaller than the cross-sectional dimension (diameter in this example) of the lumen 104 to secure placement of the cartridge 150 within the lumen 104.

FIG. 3 shows interior components of the body 102, including a piston 190 disposed towards the proximal end of the lumen 104, towards the handle 110. The piston 190 has a distal projection 192 such that the distal end of the piston 190 has a stepped configuration. The piston 190 may be biased towards the proximal end of the lumen 104 via a spring 195. The piston 190 is coupled to the actuator 105 and a shaft 197 to allow the actuator 105 initiate and control longitudinal movement of the piston 190 and shaft 197 distally along the lumen 104. While actuator 105 is shown in the form of a trigger, actuator 105 may be in any other suitable form, such as a button, a switch, or any other suitable actuator capable of engaging the piston 190.

The medical device 100 may include electronic components to control various operations of the device 100, such as operation of the motor 145 and/or an indicator 180. The medical device 100 may include a power source such as a battery 170 (e.g., a rechargeable battery) and/or may include an electronic connection 177 to receive power from an external power source and/or recharge the battery 170. The device 100 also may include a circuit board 175 with a processor, memory, etc., programmed to control the motor 145 and/or indicator 180, the electronic components being electrically connected through wires 147. When the device 100 is configured to operate automatically, the circuit board 175 may store one or more algorithms (e.g., in a memory) to control operation of the motor 145 and/or indicator 180. In some examples, the algorithm(s) may control movement of the piston 190 when initiated by the actuator 105.

Figure 4A:
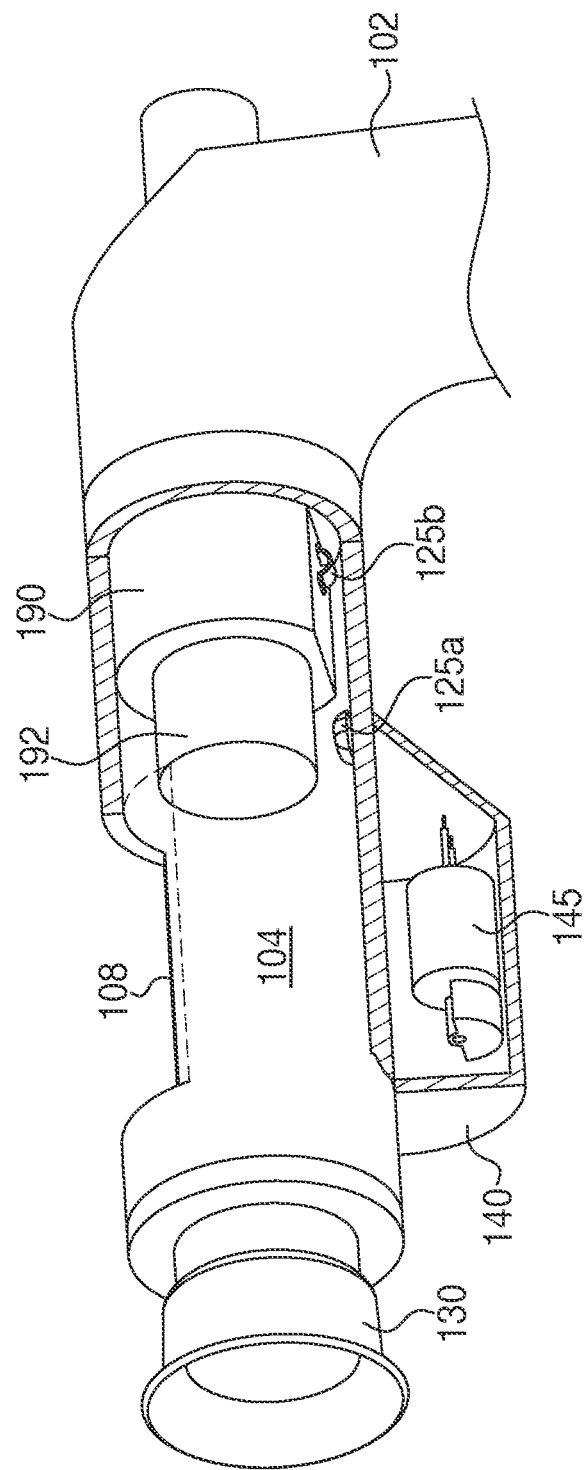
FIGS. 4A and 4B show partial cross-sectional views of components of the device of FIG. 1.
Figure 4B:
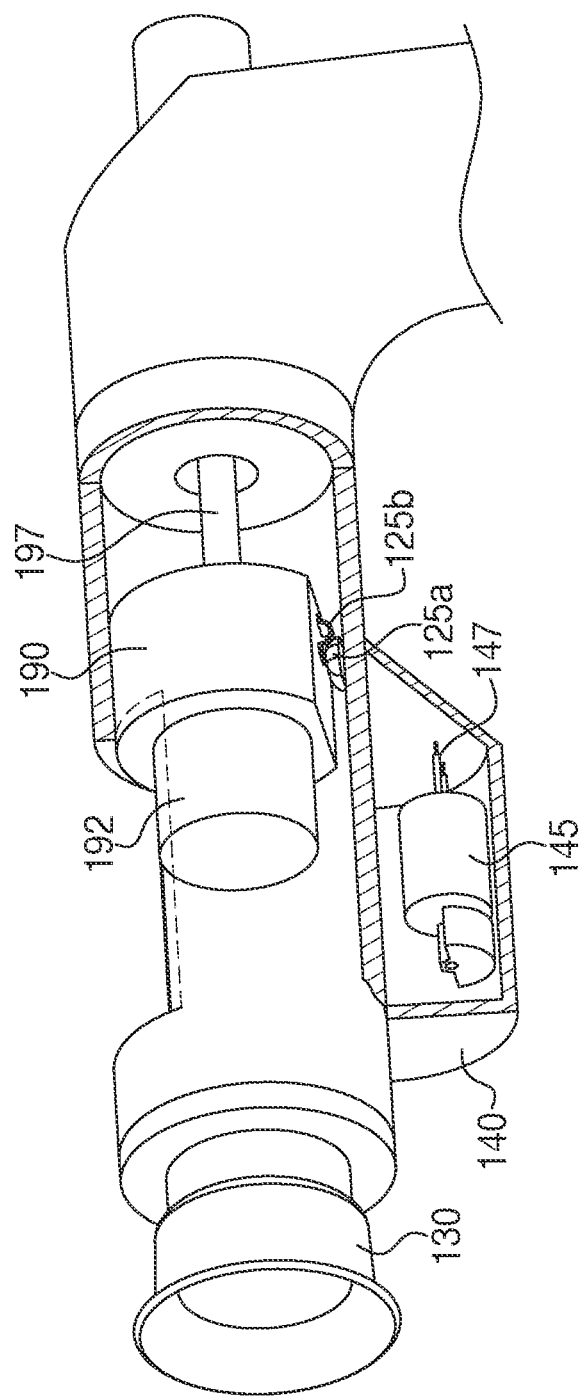

As shown in FIGS. 3, 4A, and 4B, the device 100 may include first and second electrical contacts 125a, 125b. The first electrical contact 125a may be coupled to the body 102, e.g., to an inner surface of the lumen 104 adjacent to the piston 190. The second electrical contact 125b may be coupled to the piston 190. Because the piston 190 is moveable along the lumen 104, the electrical contacts 125a, 125b may be selectively in contact with each other or separated, depending on the position of the piston. FIGS. 3 and 4A show an initial position of the piston 190 wherein the second electrical contact 125b is separated from, and distal to, the first electrical contact 125a. As the piston 190 moves distally, the second electrical contact 125b may touch the first electrical contact as shown in FIG. 4B to thereby complete the circuit. Once the circuit is completed, this may connect the motor 145 to the circuit board 175 and power source (e.g., battery 170 and/or an external power source). The motor 145 thus may be initiated to provide a shaking motion within chamber 140 and lumen 104, e.g., to promote mixing of the contents of cartridge 150 when cartridge is disposed within the lumen 104. In some examples, the motor 145 may be operated for a predetermined amount of time, such as from about 1 second to about 30 seconds, from about 5 seconds to about 20 seconds, or from about 10 seconds to about 15 seconds. Alternatively, a user may start and stop operation of the motor 145, e.g., via an actuator such as actuator 105 or a second actuator.

As shown in FIG. 3, the body 102 may include one or more openings 128 proximate a distal end of the body 102. The opening(s) 128 may have sharp edges 138 facing towards the lumen 104. The cartridge 150 may interact with the sharp edges 138 when the cartridge 150 is within the lumen 104 and moved to a distal position by the piston 190. When the piston 190 pushes the cartridge 150 distally towards the opening(s) 128, the sharp edges 138 may puncture the distal end of the cartridge 150 to allow a composition within the cartridge 150 to exit the device 100 through the opening(s) 128 and through the fitting 130.

Figure 5:
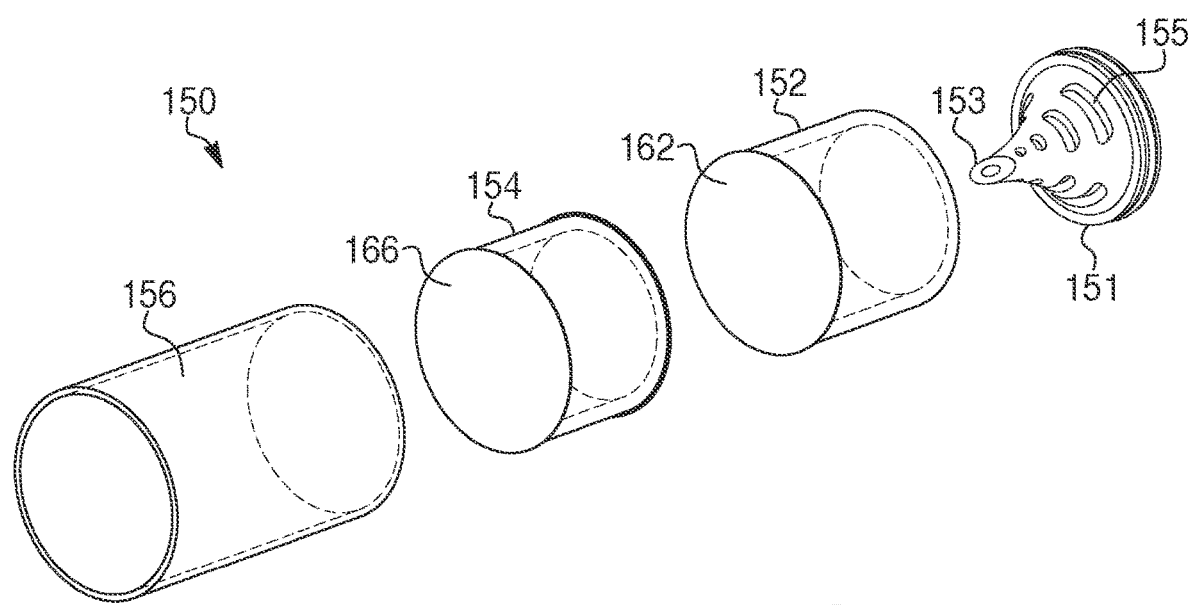
FIGS. 5 and 6 show a cartridge of the device of FIG. 1.
Figure 6:
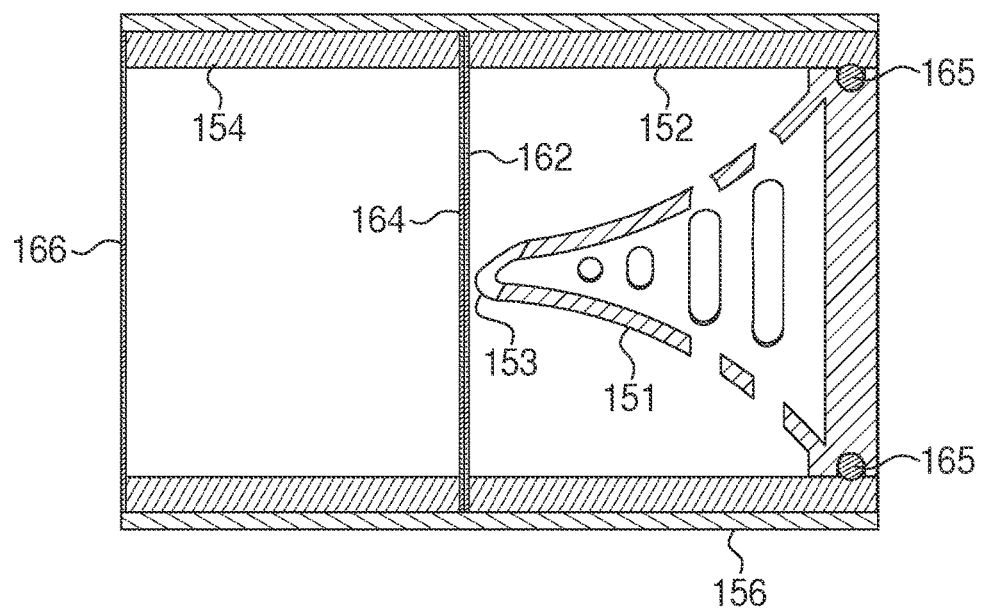

FIGS. 5 and 6 show components of the cartridge 150, including a first subcartridge 152, a second subcartridge 154, an outer container 156 around the first and second subcartridges 152, 154, and a piercing element 151. The first subcartridge 152, second subcartridge 154, outer container 156, and piercing element each may comprise a suitable materials such as a polymer or metal.

Each of the first and second subcartridges 152, 154 is generally cylindrical in shape with sealed proximal and distal ends. The proximal end of the first subcartridge is enclosed by the piercing element 151, which provides a seal with the wall of the first subcartridge 152 via a sealing element 165. For example, the sealing element 165 may include an O-ring that fits within a groove of the piercing element 151 and against the wall of the first subcartridge 152. The distal end 162 of the first subcartridge 152 is sealed with a material capable of being pierced or punctured. The material may comprise, for example a thin film of metal, metal alloy, or polymer. In at least one example, the material comprises a metallic foil. The second subcartridge 154 may include a proximal end 164 and a distal end 166 each sealed with a material capable of being pierced or punctured. The material may comprise, for example a thin film of metal, metal alloy, or polymer, such as a metallic foil. When the cartridge 150 is assembled and before use, the first and second subcartridges 152, 154 may be adjacent each other, such that the distal end 162 of the first subcartridge 152 is adjacent to the proximal end 164 of the second subcartridge 154. The distal end 166 of the second subcartridge 154 may form the distalmost end of the cartridge 150. Or in some examples, the distal end of the outer container 156 may be sealed with a material capable of being pierced or punctured, adjacent to the material of the distal end 166 of the second subcartridge 154. The piercing element 151 may have a distal-facing piercing tip 153 and one or more apertures 155. When the cartridge 150 is assembled and before use, the piercing element 151 may extend distally towards the distal end 162 of the first subcartridge 152, wherein the piercing tip 153 is proximate but not in contact with the distal end 162.

In an exemplary procedure, a user (e.g., a medical professional) may obtain the cartridge 150, the fitting 130, and device body 102 as separate components that can be assembled by coupling the fitting 130 to the body 102 and inserting the cartridge 150 into the slot 108 of the body 102 as discussed above. For example, the user may select the appropriate cartridge 150 that contains the desired composition and active agent(s), including dosage of active agent(s), and the desired size and shape of fitting 130, to suit a particular subject. In other examples, the device may be obtained in assembled form, wherein the fitting 130 is coupled to or integrated into the body 102, and the cartridge 150 is inserted into the lumen 104 of the body 102. In the initial position, the proximal end of the cartridge 150 (corresponding to the proximal end of the piercing element 151) may be adjacent to, and in contact with, the projection 192 of the piston 190. Due to the stepped configuration of the piston 190, the projection 192 may contact the piercing element 151 without contacting the wall of the first subcartridge 152. This initial position of the piston 190 is illustrated in FIG. 4A, wherein the first and second electrical contacts 125a, 125b are separated from each other.

The user may press the actuator 105 to engage the shaft 197 and cause the piston 190 to move distally, moving the piercing element 151 relative to the first subcartridge 152 and the rest of the cartridge 150. The body 102 includes an internal stop that prevents further movement of the piston 190 when the actuator 105 contacts the stop. As the piercing element 151 moves, the piercing tip 153 may have a sharp surface that pierces or punctures the material of the distal end 162 of the first subcartridge 152. By breaking the seal of the first subcartridge 152, the first and second subcartridge 152, 154 may be in fluid communication with each other. For example, the first subcartridge 152 may contain a liquid such as a buffer solution able to enter the second subcartridge 154 to combine with agent(s) contained within the second subcartridge 154. This position of the piston 190 is illustrated in FIG. 4B, wherein the first and second electrical contacts 125a, 125b are in contact. As a result, the motor 145 may be activated for a predetermined or desired amount of time to shake the cartridge 150 and promote mixing of the liquid and the agent(s) to produce a composition ready for administration to the eye.

The user may press the actuator 105 a second time to engage the shaft 197 a second time and move the piston 190 further distally. At this point, the stepped portion of the piston 190 contacts the wall of the cartridge 150 to move the entire cartridge 150 distally to contact the sharp edges 138 at the end of the lumen 104. The sharp edges 138 may pierce or puncture the material of the distal end 166 of the second cartridge 154 (as well as material of the distal end of the outer container 156, if present) to allow the composition therein to exit the cartridge 150 through the opening(s) 128 and through the fitting 130. The user may press the actuator 105 a second time after placing the fitting 130 on the subject's eye. The subject may be facing upward when the fitting 130 contacts the subject's eye, so that the force of gravity causes the composition to exit through the opening(s) 128 and come into contact with the cornea of the eye, the composition being kept in contact with the eye via the enclosed space provided by the fitting 130 (between the fitting 130 and the surface of the cornea). The volume provided by this enclosed space may range from about 0.5 mL to about 5 mL; for example, the amount of composition applied to the eye may range from about 0.5 mL to about 5 mL, or from about 1 mL to about 3 mL. The composition may be held in contact with the eye via the device 100 for at least 30 seconds, such as 30 seconds to 60 seconds or 30 seconds to 45 seconds. Once the desired amount of time has passed to deliver and/or expose the eye to the composition, the user may remove the device and flush the subject's eye with a buffer solution or other suitable eye wash. When the user is treating both eyes of the subject, the user may remove the used cartridge 150 and insert a new cartridge, and repeat the steps above to treat the second eye.

Figure 7:
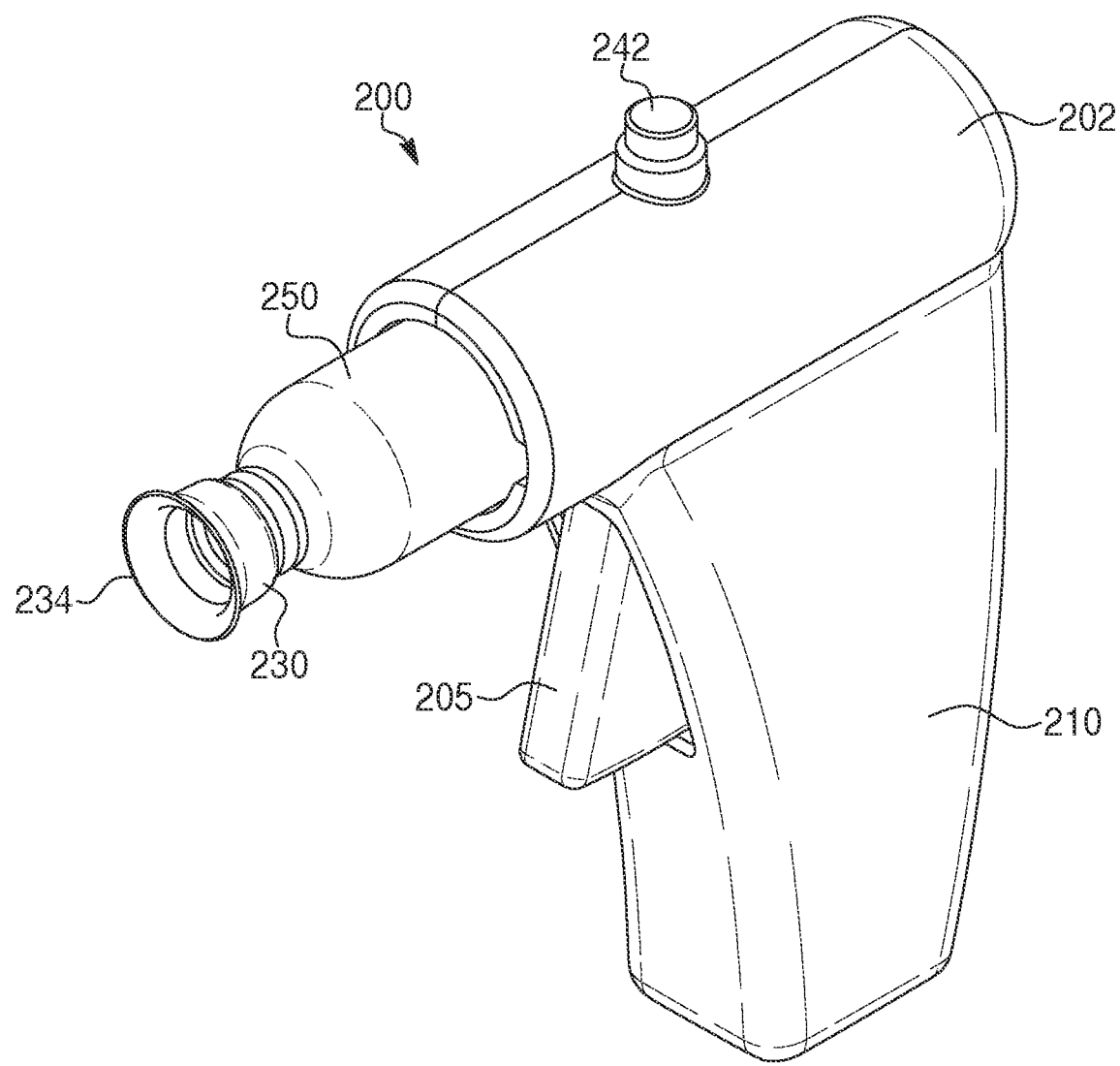
FIG. 7 is a perspective view of another exemplary medical device according to some aspects of the present disclosure.
Figure 8A:
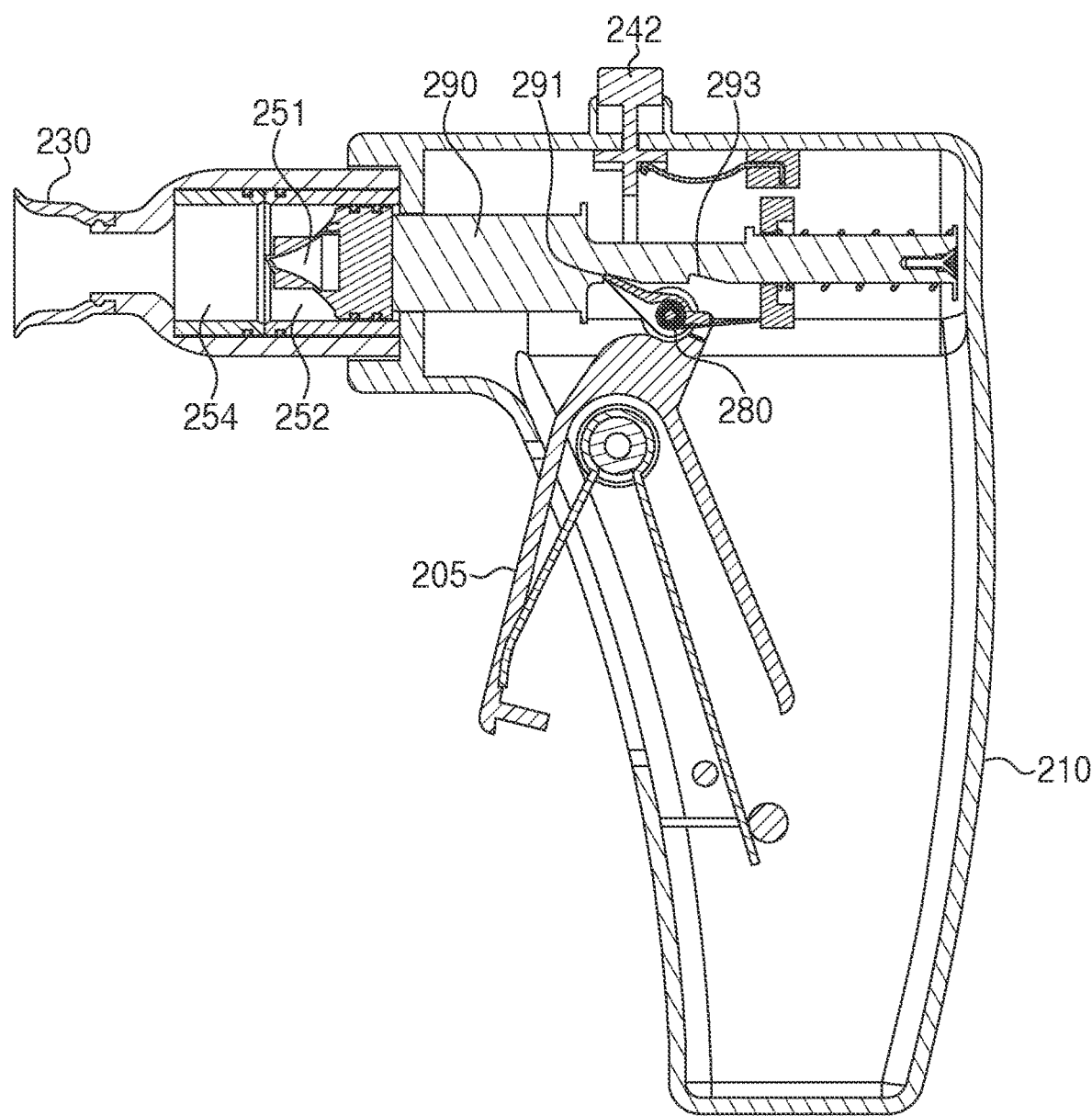
FIGS. 8A and 8B are side cross-sectional views of the device of FIG. 7 in a first position.
Figure 8B:
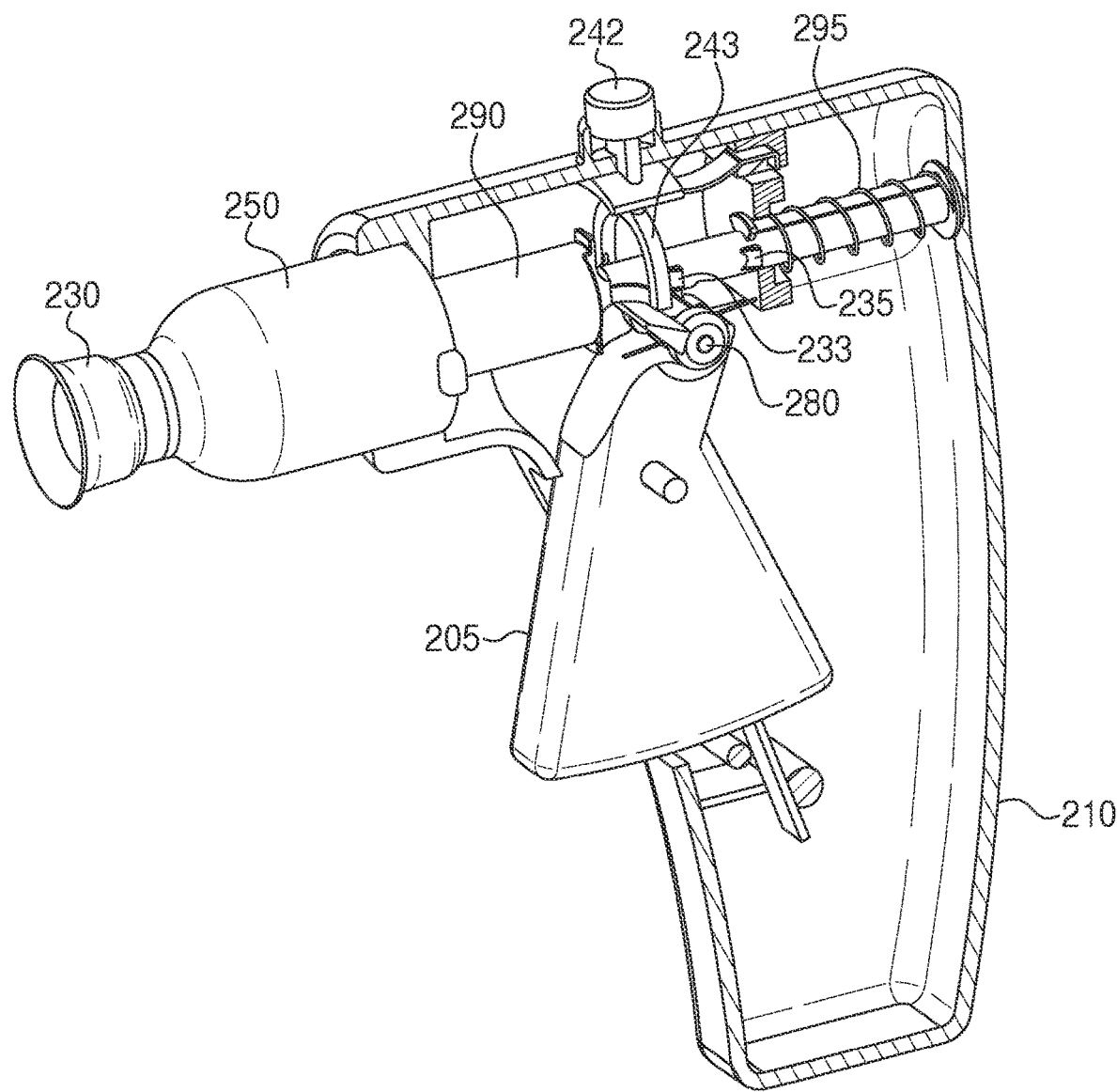
Figure 9:
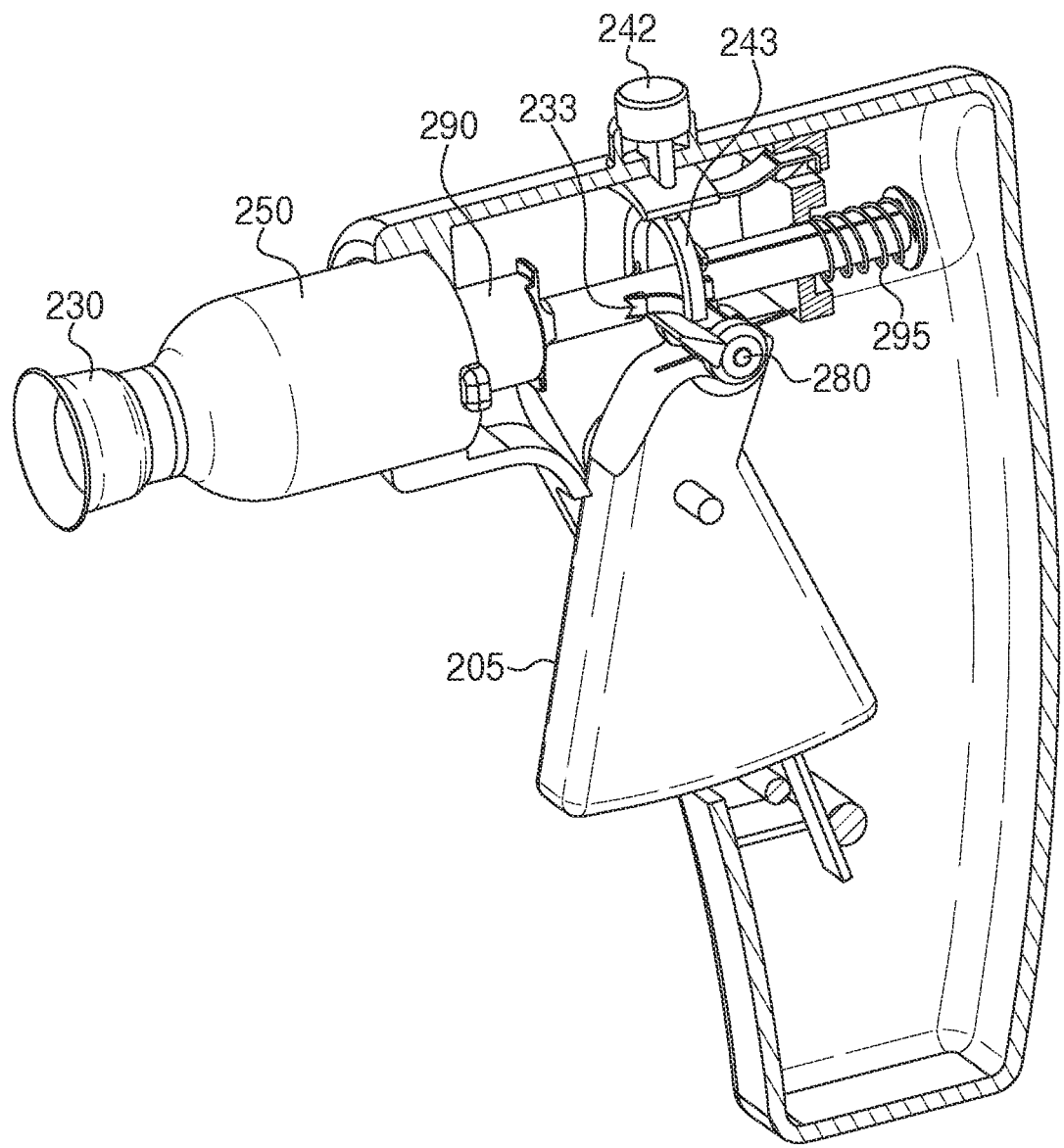
FIG. 9 is a side cross-sectional view of the device of FIG. 7 in a second position.

FIGS. 7-11 illustrate another exemplary medical device 200 according to aspects of the present disclosure. Except for the variations described below, the device 200 may include any of the features of device 100. As shown in FIG. 7, the device 200 includes a body 202 with a housing that includes a handle 210 and an actuator 205. While the actuator 205 is shown in the form of a trigger, it may be in any other suitable form, such as a button, a switch, or any other suitable actuator capable of causing movement of a piston 290 as discussed below. The body 202 defines a lumen that receives a piston 290. The body 202 receives a cartridge 250 (e.g., via a distal slot in communication with the lumen), where cartridge 250 may include any of the features of cartridge 150 of FIGS. 1-6. The cartridge 250 may be removable and replaceable, for example, and may be preloaded with one or more active agents.

Figure 10:
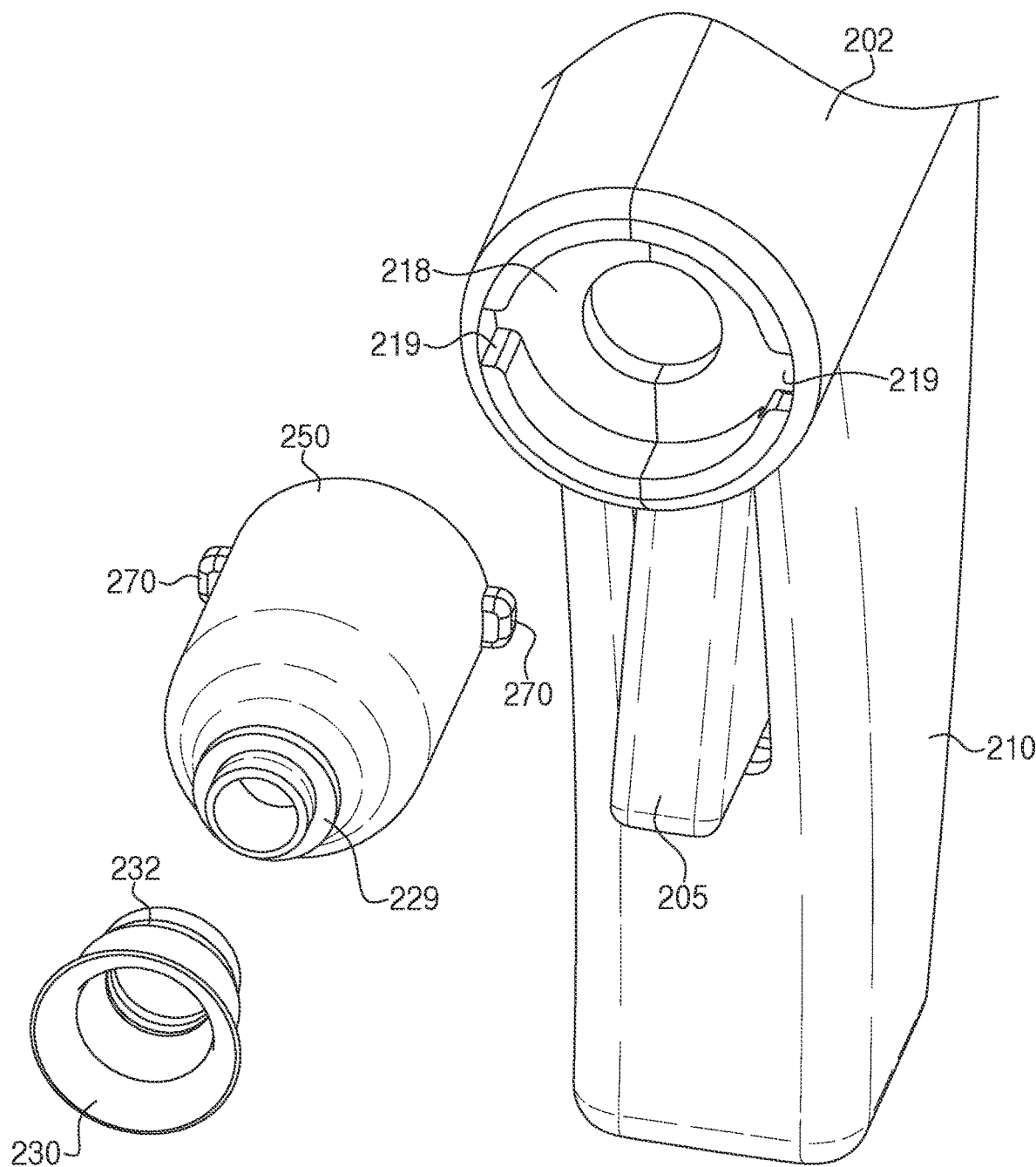
FIG. 10 shows an exploded view of components of the device of FIG. 7.
Figure 11:
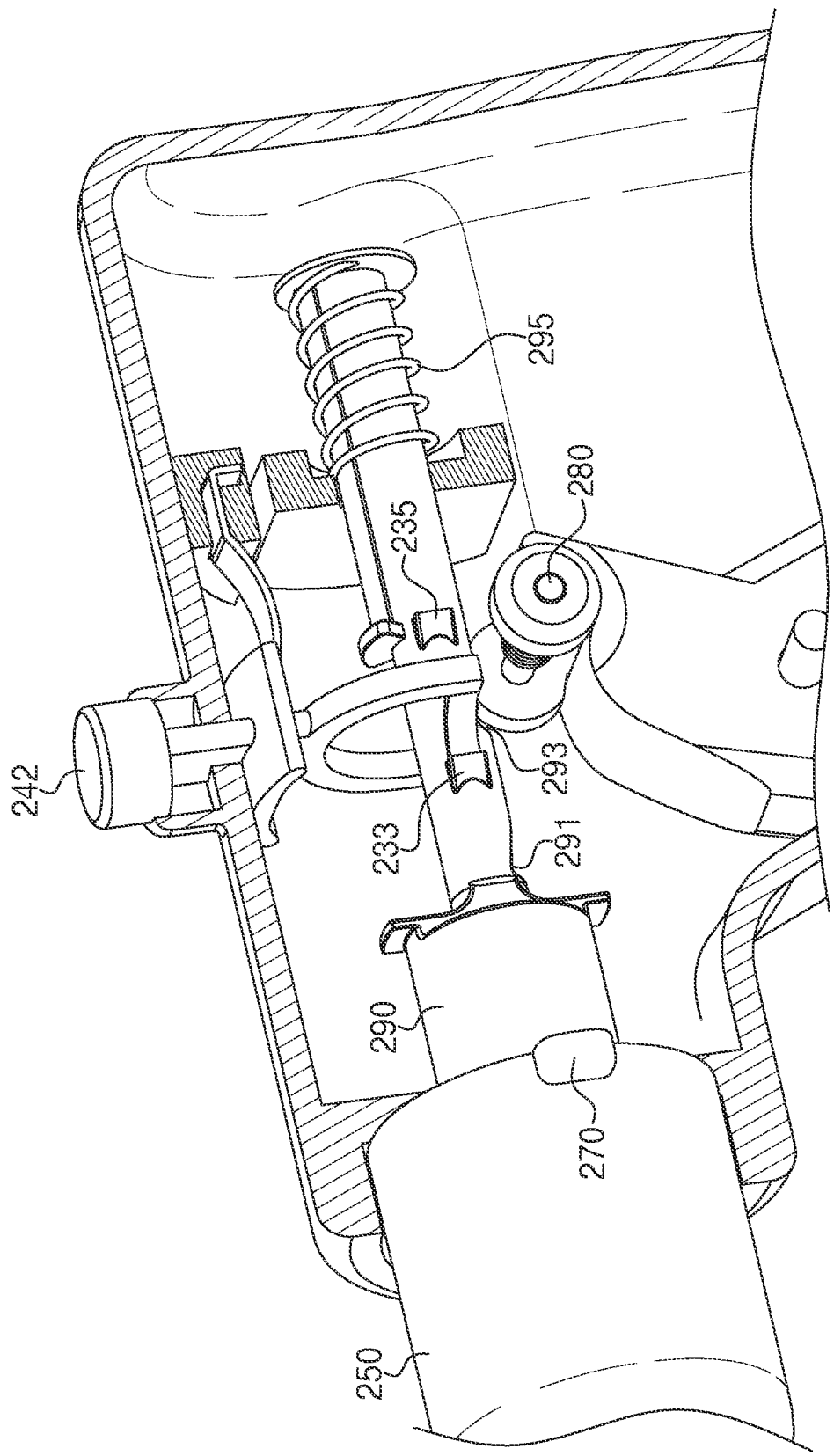
FIG. 11 is a side cross-sectional view of a portion of the device of FIG. 7.

The device 200 also includes a fitting 230, which may include any of the features of fitting 130 of FIGS. 1-4B. For example, the fitting 230 may be flexible and have a flared distal end 234 that is able to accommodate the convex curvature of a subject's eye. The fitting 230 may include engagement elements 232 such as clips, tabs, friction-fit, Luer-lock connection, magnets, etc., complementary to engagement elements 229 of the cartridge 250, e.g., located at or proximate the distal end of cartridge 250. As shown in FIG. 10, the engagement elements 229, 232 may provide for a friction-fit connection, wherein a groove 232 on an inner surface of the fitting 230 receives a raised lip on the outer surface of the distal end of the cartridge 250. The fitting 230 may be flexible in order to allow it to establish a tight friction-fit seal with the cartridge 250. In at least one example, the fitting 230 comprises a biocompatible rubber or flexible plastic.

As mentioned above, the cartridge 250 may have similar features as cartridge 150 of FIG. 1. For example, the cartridge 250 may include a first subcartridge 252, a second subcartridge 254, and a piercing element 251 (see FIG. 8A). The first subcartridge 252, second subcartridge 254, and piercing element 251 each may comprise suitable materials such as a polymer or metal. The piercing element 251 includes a piercing tip similar to piercing tip 153 of cartridge 150. Proximal and distal ends of the first and second subcartridges 252, 254 may be sealed with a material capable of being pierced or punctured. The material may comprise, for example a thin film of polymer, metal, or metal alloy, such as a metallic foil.

The device 200 includes a mechanism for advancing the piston 290 to press against the proximal end of the cartridge 250 in sequential steps to mix the contents of the subcartridges 252, 254 together to form a therapeutic composition, and then to release the composition from the cartridge 250 and administer the composition to a subject (e.g., a patient). The mechanism includes a piston 290 coupled to a cam 280, the piston 290 being biased in the proximal direction, away from the cartridge 250, via a spring 295. In a starting or ready position of the device 200 (FIGS. 8A-8B), the piston 290 is in a proximal-most position and prevented from moving distally by the cam 280 being disposed in the first (distal) notch 291. The lower surface of the piston 290 includes two notches 291, 293 for receiving the cam 280, and each side of the piston 290 includes two pockets 233, 235 for receiving arms of an extension 243.

In an exemplary procedure, the user may couple the fitting 230 to the cartridge 250, and then insert the cartridge 250 into the body 202 so that the two tabs 270 of the cartridge 250 are received within corresponding recesses 219 of the body 202, the recesses being defined within a distal surface 218 that includes the slot for receiving the cartridge 250. The user may rotate the cartridge 250 to lock the tabs 270 in place within the recesses 219. Alternatively, the user may insert the cartridge 250 into the body 202 and lock the cartridge 250 in place by rotation, and then couple the fitting 230 to the cartridge 250. When first assembled, the device 200 is in a first, starting position with the cam 280 resting in the distal notch 291 of the piston 290, and the distal end of the piston in contact with the proximal sealed end of the cartridge 250 adjacent to the first subcartridge 252.

Upon a first activation of the actuator 205 by a user, the actuator 205 rotates to cause a corresponding rotation of the cam 280 that pushes the cam 280 in the notch 291 against the piston 290. This moves the piston 209 distally until the cam 280 reaches its full longitudinal length and cannot push the piston 290 further. At this point, each arm of the extension 243 is positioned so as to be received within a corresponding pocket 233. Each pocket 233 has a closed distal end, so that once the respective arms are received in the pockets 233, the arms act as an internal stop to prevent proximal movement of the piston 290. Thus, once the user releases the actuator 205 to cause the cam 280 to release from the notch 291, the arms of the extension 243 fit within the pockets 233 to maintain the position of the piston 290 relative to the cartridge 250. At this point, the cam 280 fits within the second (proximal) notch 293 (see FIGS. 9 and 11).

This first longitudinal movement of the piston 290 (via a first activation of the actuator 205) corresponds to a first movement of the piercing element 251 of the cartridge 250 distally relative to the remainder of the cartridge 250. The piercing tip of the piercing element 251 punctures the walls separating the first and second subcartridges 252, 254. The agents(s) contained in the first subcartridge 252 (e.g., a buffer solution optionally with one or more active agents combined with the buffer solution) may then mix with the agent(s) contained in the second subcartridge 254 (e.g., an acylating agent and/or other active agents) to form a therapeutic composition. Because the arms of the extension 243 disposed within the pockets 233 serve as a stop, the piston 290 is prevented from moving the piercing element 251 further. The distalmost end of the cartridge 250 remains sealed, such that the composition remains contained within the cartridge 250.

The user may wait a suitable amount of time sufficient to ensure adequate mixing of agents in the cartridge 250 to form the composition. For example, the user may wait a pre-determined time to allow the agents to mix and achieve the appropriate pH. Next, the user may apply the fitting 230 to the subject's eye so that the flared distal end 234 of the fitting 230 contacts the eye. The use then may activate the actuator 205 a second time, again rotating the actuator 205 relative to the handle 210. This causes a corresponding rotation of the cam 280 that pushes the cam 280 in the second notch 293 against the piston 290. This moves the piston 209 distally until the cam 280 again reaches its full longitudinal length and cannot push the piston 290 further. At this point, each arm of the extension 243 is positioned so as to be received within a corresponding pocket 235. Like distal pockets 233, each proximal pocket 235 has a closed distal end, so that once the respective arms are received in the pockets 235, the arms act as an internal stop to prevent proximal movement of the piston 290. This second longitudinal movement of the piston 290 (via a second activation of the actuator 205) corresponds to a second movement of the piercing element 251 distally relative to the remainder of the cartridge 250. The piercing tip of the piercing element 251 punctures the distalmost end of the cartridge 250 to allow the composition to exit the device 200. The subject may be facing upward when the fitting 230 contacts the subject's eye, so that the force of gravity causes the composition to exit through the fitting 230 and come into contact with the cornea of the eye, the composition being kept in contact with the eye via the enclosed space provided by the fitting 230 (between the fitting 130 and the surface of the cornea). Once sufficient time has passed to allow the composition to treat the eye, the user may remove the device 200 and optionally wash the subject's eye with buffer solution.

At this point, the unsealed cartridge 250 is used and may be removed from the body 202 of the device to be disposed. The user may rotate the cartridge 250 to release the tabs 270 from the corresponding recesses 219 of the body 202. In order to re-set the position of the piston 290, the user may press a release button 242. The release button 242 is coupled to the extension 243 (see FIG. 11; part of the cam 280 being omitted for illustrative purposes), such that pressing the release button 242 pushes the extension 243 and arms thereof downward. Each pocket 235 has an open bottom end, such that the arms are released from the constraints of the pockets 235 to allow the piston 290 to move proximally by virtue of the bias provided by spring 295. The piston 290 thereby returns to its starting position (FIGS. 8A-8B), with the body 202 of the device able to receive a new cartridge.

The components of the devices herein may be provided in a kit. For example, a kit according to the present disclosure may include a device body (e.g., body 102 or body 202), one or more cartridges (e.g., cartridge 150 or cartridge 250), and one or more fittings (e.g., fitting 130 or fitting 230). Kits according to the present disclosure may include a plurality of fittings of different sizes to accommodate different subjects. For example, an exemplary kit may include a device body, a cartridge, and two or more fittings of different sizes, each fitting including engagement elements complementary to engagement elements of the cartridge. In this way, the user may select the appropriate fitting or exchange for different fittings, depending on the size suitable for a given subject's eye. In some examples, the kit may include two or more cartridges. For example, an exemplary kit may include a device body, at least two cartridges insertable into, and removable from, the device body, where the at least two cartridges may be preloaded with the same active agent(s) and/or different active agent(s). The user may be able to treat both eyes of a subject with a single device, removing a used cartridge and replacing it with a new cartridge for treating the second eye after the first eye has been treated. In some examples, the kit may include cartridges that include different active agents to allow a user to treat the same eye or different eyes with different active agents, using the same device.

The devices herein may provide for effective and controlled delivery of therapeutic compositions to the eye(s) of a subject. For example, the devices and methods herein may be useful for delivery of pH-sensitive compositions to the eye to open trans-epithelial channels for effective delivery of other active agents. In some examples, the pH-sensitive composition also includes the other active agent(s).

As discussed above, the cartridge may include two or more subcartridges, each subcartridge being sealed prior to use to avoid environmental contamination or other environmental exposure that may damage, inactivate, or otherwise impair activity of the active agent(s) before administration to the subject. The cartridge may be configured for single use, wherein each subcartridge includes the desired amount of agent (e.g., buffer solution or active agent) for a single step administration to the eye. In this way, the devices herein may be used to administer therapeutic compositions in the absence of preservatives that could irritate or even damage ocular tissue. Further, the cartridge may be pre-loaded with the desired amount of active agent for targeted delivery to the eye, avoiding overdosing and potentially toxic amounts of active agent that otherwise could be provided in a multi-dosing regimen.

As mentioned above, various active agents may be administered simultaneously or substantially simultaneously with opening tight epithelial junctures of the cornea by delivering a composition comprising an acylating agent, a buffer solution, and the active agent. According to some aspects of the present disclosure, the active agent may comprise a medication for an eye condition, such medications including but not limited to riboflavin, timolol, latanoprost, epinephrine, neosynephrine, phenylephrine, hydroxyamphetamine, tropicamide, cyclopentolate, atropine, homatropine, and scopolamine. For example, riboflavin may be administered to treat keratoconus by ultraviolet (UVA) exposure following administration of the riboflavin. In some examples, the active agent comprises a steroid, an anti-inflammatory agent, an antihistamine, a prostaglandin, an anesthetic agent, or an antimicrobial agent (e.g., an antifungal agent, an antibiotic, an antibacterial agent, or an antiviral agent).

In an exemplary procedure, a cartridge may be selected comprising a first subcartridge that contains a buffer solution (e.g., sodium phosphate buffer) and an active agent (e.g., 1.0% tropicamide), and a second subcartridge that contains an acylating agent such as glutaric anhydride. For example, the second subcartridge may contain from about 3 mg to about 10 mg, e.g., about 5 mg, of glutaric anhydride in powder form or as a solid layer on an inner surface of the second subcartridge. When the first and second subcartridges are in fluid communication by operating the device as discussed above, the acylating agent may combine with the buffer and active agent to produce a therapeutic composition comprising the acylating agent and the active agent. Over time, such as within the first several seconds to a minute, the pH of the composition may decrease. When the pH is between about 8.4 and 8.6, the composition may be suitable for delivery to the subject's eye. The user may monitor the amount of time that has passed once the contents of the subcartridges have been combined and/or the user may use an indicator of the device (e.g., indicator 180 of device 100) to determine when the composition has reached the desired pH.

After the composition has been applied to the subject's eye, the user may remove and disregard the cartridge. A new cartridge (preloaded with the same buffer, acylating agent, and active agent) may be inserted into the device to treat the subject's other eye in the same fashion, after which the second cartridge likewise may be removed and disregarded. The body of the device may be sterilized between uses and/or between treating different subjects.

The present application encompasses additional procedures for delivering therapeutic agents to the eye. For example, in cataract procedures, a medical professional may use the devices herein to administer an antibiotic and/or an anti-inflammatory agent (e.g., deflazacort or other anti-inflammatory agent) to a patient to prepare the patient for surgery, rather than applying drops. Additionally or alternatively, after a cataract procedure or other surgical procedure, a medical professional may administer an antibiotic and/or a steroid (e.g., prednisone or other steroid) using the devices herein, rather than by injection. The methods and devices herein may be used to saturate the cornea with an antibiotic, steroid, and/or anti-inflammatory agent where indicated in a single application as part of a pre-operative preparation, and then have these active agents continue to be present at therapeutic levels post-surgery.

It is intended that the specification and examples be considered as exemplary only, with a true scope and spirit of the present disclosure being indicated by the following claims.

The invention claimed is:

1. A method of treating a subject using a medical device comprising a housing and a flexible fitting, wherein the housing defines a lumen that contains a cartridge and a piston operably coupled to an actuator, and wherein the cartridge includes a first subcartridge that contains a buffer solution and a second subcartridge that contains an active agent, the method comprising:
    preparing a composition by combining the buffer solution with the active agent by pressing the actuator of the device to move the piston distally to establish fluid communication between the first subcartridge and the second subcartridge;
    mixing the composition, wherein a pH of the composition decreases over time;
    placing the fitting against an eye of the subject, wherein the fitting flares radially outward to accommodate a convex curvature of the eye; and
    administering the composition to the eye by expelling the composition into an enclosed space between the fitting and the eye.

2. The method of claim 1, wherein the active agent is an acylating agent and the composition is administered to the eye while having a pH ranging from about 8.4 to about 8.6.

3. The method of claim 2, wherein the active agent is a first active agent and the first subcartridge further comprises a second active agent mixed with the buffer solution, and wherein the second active agent comprises a steroid, an anti-inflammatory agent, an antihistamine, a prostaglandin, an anesthetic agent, or an antimicrobial agent.

4. The method of claim 1, wherein the composition does not comprise a preservative.

5. The method of claim 1, wherein establishing fluid communication between the first subcartridge and the second subcartridge includes piercing a thin foil or polymeric film between the first subcartridge and the second subcartridge.

6. The method of claim 1, further comprising inserting the cartridge into the lumen before preparing the composition, and removing the cartridge from the lumen after administering the composition to the eye.

7. The method of claim 1, wherein the housing includes an indicator in the form of a light source configured to emit light a predetermined amount of time after the actuator is pressed to signal that the composition has reached a pH suitable for application to the eye of the subject.

8. The method of claim 7, wherein administering the composition to the eye occurs after the light source emits light at the predetermined amount of time.

9. The method of claim 6, wherein the housing includes a release button and the method further comprises:
    removing the cartridge from the lumen after administering the composition to the eye; and
    re-setting a starting position of the piston by pressing the release button to withdraw arms coupled to the release button from pockets of the piston, such that the piston moves proximally.

10. A method of treating a subject using a medical device comprising a housing and a flexible fitting, wherein the housing defines a lumen that contains a cartridge and a piston operably coupled to an actuator, and wherein the cartridge includes a first subcartridge that contains a buffer solution and an active agent, and a second subcartridge that contains an acylating agent, the method comprising:
    preparing a composition by pressing the actuator of the device to move the piston distally to establish fluid communication between the first subcartridge and the second subcartridge and thereby combine the buffer solution and the active agent with the acylating agent, wherein pressing the actuator initiates a predetermined time interval;
    at an end of the predetermined time interval, placing the fitting against an eye of the subject, wherein the fitting flares radially outward to accommodate a convex curvature of the eye; and
    administering the composition to the eye by expelling the composition into an enclosed space between the fitting and the eye.

11. The method of claim 10, wherein the housing includes an indicator that provides an audio or visual signal at the end of the predetermined time interval.

12. The method of claim 10, wherein the active agent comprises a steroid, an anti-inflammatory agent, an antihistamine, a prostaglandin, an anesthetic agent, or an antimicrobial agent.

13. The method of claim 10, wherein the composition has a pH ranging from about 8.4 to about 8.6 at the end of the predetermined time interval.

14. The method of claim 10, wherein the housing includes a release button and the method further comprises:
    removing the cartridge from the lumen after administering the composition to the eye; and
    re-setting a starting position of the piston by pressing the release button to withdraw arms coupled to the release button from pockets of the piston, such that the piston moves proximally.

15. The method of claim 14, wherein the piston includes two pockets on opposing lateral sides of the piston.

16. The method of claim 10, wherein the composition is held in contact with the eye for at least 30 seconds.

\* \* \* \* \*